(12) United States Patent
Zhang et al.

(10) Patent No.: US 10,998,090 B2
(45) Date of Patent: May 4, 2021

(54) METHOD AND TERMINAL FOR ANALYZING DRUG-DISEASE RELEVANCE RELATION, NON-TRANSITORY COMPUTER-READABLE STORAGE MEDIUM

(71) Applicant: BOE TECHNOLOGY GROUP CO., LTD., Beijing (CN)

(72) Inventors: Zhenzhong Zhang, Beijing (CN); Hui Li, Beijing (CN); Chenyin Shen, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 326 days.

(21) Appl. No.: 15/952,582

(22) Filed: Apr. 13, 2018

(65) Prior Publication Data
US 2019/0035494 A1 Jan. 31, 2019

(30) Foreign Application Priority Data
Jul. 31, 2017 (CN) .......................... 201710642650.X (51) Int. Cl.
*G16H 20/10* (2018.01)
*G06F 17/16* (2006.01)
*G16H 70/40* (2018.01)

(52) U.S. Cl.
CPC ............. *G16H 20/10* (2018.01); *G06F 17/16* (2013.01); *G16H 70/40* (2018.01)

(58) Field of Classification Search
CPC ........ C12Q 2600/136; C12Q 2600/106; G01N 33/6896; G01N 2500/04; G01N 33/5023; G01N 2800/50; G01N 2800/52; G16H 10/60; G16H 20/10; G16H 50/30; G16H 50/50; G16H 50/70; G16H 70/40; G16H 10/20; G16H 50/20; G06F 19/3456
See application file for complete search history.

(56) References Cited

U.S. PATENT DOCUMENTS

2012/0078526 A1* 3/2012 Avinash ................ G16H 50/70
702/19

FOREIGN PATENT DOCUMENTS

CN 104021316 A 9/2014
CN 105653846 A 6/2016

OTHER PUBLICATIONS

Wang, H. et al., "Mining Drug-Disease Relationships as a Complement to Medical Genetics-Based Drug Repositioning: Where a Recommendation System Meets Genome-Wide Association Studies," Clinical Pharmacology & Therapeutics, vol. 97, No. 5, May 2015.
Cheng, F. et al., "Adverse Drug Events: Database Construction and in Silico Prediction," Journal of Chemical Information and Modeling, American Chemical Society, 2013, vol. 53, pp. 744-752.
(Continued)

*Primary Examiner* — Maroun P Kanaan
(74) *Attorney, Agent, or Firm* — McDermott Will & Emery LLP (57) ABSTRACT

A terminal for analyzing a drug-disease relevance relation includes a transceiver and a processor. The transceiver is configured to receive drug information, disease information and drug-disease relevance relation information. The processor is configured to construct a pharmacodynamic relation model based on the drug information, the disease information and the drug-disease relevance relation information.

17 Claims, 4 Drawing Sheets

(56) References Cited

OTHER PUBLICATIONS

"Mining drug-disease relationships:a recommendation system," Chinese Pharmacological Bulletin; Dec. 2015; 31 (2); pp. 1770-1774; with English translation.
"Modular deconstruction of complex drug-disease networks," Chinese Pharmacological Bulletin Nov. 2013; 29 (11); 1499-1502; with English translation.
First Office Action issued in Chinese Patent Application No. 201710642650.X, dated Jun. 5, 2019; with English translation.

* cited by examiner

METHOD AND TERMINAL FOR ANALYZING DRUG-DISEASE RELEVANCE RELATION, NON-TRANSITORY COMPUTER-READABLE STORAGE MEDIUM

CROSS-REFERENCE TO RELATED APPLICATIONS

This application claims priority to Chinese Patent Application No. 201710642650.X, entitled "SYSTEM AND METHOD FOR ANALYZING DRUG-DISEASE RELEVANCE RELATION" and filed on Jul. 31, 2017, which is incorporated herein by reference in its entirety.

TECHNICAL FIELD

The present disclosure relates to a method and a terminal for analyzing a drug-disease relevance relation, and a non-transitory computer-readable storage medium.

BACKGROUND

With the development of the medical technology, many new drugs have been developed. These drugs are verified and then applied to the clinic to treat diseases, and great effect has been gained. However, there is certain side effect in the use of drugs, so that the doses of drugs need to be controlled to avoid adverse reactions in patients' bodies while ensuring the therapeutic effect.

SUMMARY

In one aspect, some embodiments of the present disclosure provide a terminal for analyzing a drug-disease relevance relation, comprising:

a transceiver, configured to receive drug information, disease information and drug-disease relevance relation information, wherein the drug-disease relevance relation information comprises at least one of drug-disease therapeutic relation information and drug-disease side-effect relation information; and a processor, coupled with the transceiver and configured to construct a pharmacodynamic relation model based on the drug information, the disease information and the drug-disease relevance relation information, wherein the pharmacodynamic relation model is configured to analyze a drug-disease relevance relation r, and the drug-disease relevance relation comprises at least one of a drug-disease therapeutic relation $r_1$ and a drug-disease side-effect relation $r_0$.

In some embodiments of the present disclosure, the processor is further configured to:

obtain a relevance score of the drug-disease relevance relation based on the pharmacodynamic relation model, to evaluate the drug-disease relevance relation.

In some embodiments of the present disclosure, the pharmacodynamic relation model comprises an evaluation function f(d,r,s) for the drug-disease relevance relation and vector space data in a real vector space, $f(d,r,s) = \|M_R \times dv - M_R \times sv - vR\|_2$;

the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, where d represents the drug, s represents the disease, $\|.\|_2$ represents L2 norm, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation; the n-dimensional column vector vR for the drug-disease relevance relation comprises an n-dimensional column vector vr for the drug-disease therapeutic relation and/or an n-dimensional column vector vs for the drug-disease side-effect relation;

an expression of the k-dimensional column vector dv for the drug, an expression of the k-dimensional column vector sv for the disease, an expression of the n-dimensional column vector vR for the drug-disease relevance relation, an expression of the n×k-dimensional mapping matrix $M_R$ for the drug-disease relevance relation, and an expression of the evaluation function f(d,r,s) for the drug-disease relevance relation are solved by optimizing a target function L;

$$L = \sum_{(di,r,sj) \in T} \sum_{(di',r,sj') \in T'} \max(0, f(di, r, sj) - f(di', r, sj') + \gamma)$$

where, $f(di, r, sj) = \|M_R \times dvi - M_R \times svj - vR\|_2$ $f(di', r, sj') = \|M_R \times dvi' - M_R \times svj' - vR\|_2$ where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max (a,b) represents an operation of taking a maximum value of a and b, and γ represents a pre-defined margin and γ≥f(di', r,sj')−f(di,r,sj).

In some embodiments of the present disclosure, a method for optimizing the target function L is a stochastic gradient descent algorithm.

In some embodiments of the present disclosure, in the real vector space, k<n and both n and k are less than the number of types of drugs in the drug information and the number of types of diseases in the disease information.

In some embodiments of the present disclosure, the dimension of the real vector space is 300-500.

In some embodiments of the present disclosure, the transceiver and the processor are configured to be selected from a group consisting of:

the transceiver is configured to receive drug information; the processor is configured to analyze the drug information according to the pharmacodynamic relation model to obtain relevance relations between a drug in the drug information and different diseases, wherein the relevance relations between the drug in the drug information and different diseases comprise therapeutic relations between the drug in the drug information and different diseases and/or side-effect relations between the drug in the drug information and different diseases; and the transceiver is configured to output the relevance relations between the drug in the drug information and different diseases, the transceiver is configured to receive disease information; the processor is configured to analyze the disease information according to the pharmacodynamic relation model to obtain relevance relations between different drugs and a disease in the disease information, wherein the relevance relations between different drugs and the disease in the disease information comprise therapeutic relations between different drugs and the disease in the disease information and/or side-effect relations between different drugs and the disease in the disease information; and the transceiver is configured to output the relevance relations between different drugs and the disease in the disease information, and the transceiver is configured to receive drug information and disease information; the processor is configured to analyze the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and the transceiver is configured to output the relevance relation between the drug in the drug information and the disease in the disease information.

In another aspect, some embodiments of the present disclosure provide a method for analyzing a drug-disease relevance relation, which comprises:

collecting drug information, disease information and drug-disease relevance relation information, wherein the drug-disease relevance relation information comprises at least one of drug-disease therapeutic relation information and drug-disease side-effect relation information; and constructing a pharmacodynamic relation model based on the drug information, the disease information and the drug-disease relevance relation information, wherein the pharmacodynamic relation model is configured to analyze a drug-disease relevance relation r, and the drug-disease relevance relation comprises at least one of a drug-disease therapeutic relation $r_1$ and a drug-disease side-effect relation $r_0$.

In some embodiments of the present disclosure, constructing a pharmacodynamic relation model based on the drug information, the disease information and the drug-disease relevance relation information, comprises:

mapping the drug information, the disease information and the drug-disease relevance relation information to a real vector space to obtain vector space data, wherein the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, the n-dimensional column vector vR for the drug-disease relevance relation comprises an n-dimensional column vector vr for the drug-disease therapeutic relation and/or an n-dimensional column vector vs for the drug-disease side-effect relation, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation;

constructing an evaluation function f(d,r,s) for the drug-disease relevance relation according to the vector space data, and f(d,r,s)=$\|M_R \times dv - M_R \times sv - vR\|_2$, where d represents the drug, s represents the disease, and $\|.\|2$ represents L2 norm;

setting a target function L according to the evaluation function f(d,r,s) for the drug-disease relevance relation, $$L = \sum_{(di,r,sj) \in T} \sum_{(di',r,sj') \in T'} \max(0, f(di, r, sj) - f(di', r, sj') + \gamma)$$

where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max (a,b) represents an operation of taking a maximum value of a and b, and γ represents a pre-defined margin and y≥f(di', r,sj')−f(di,r,sj);

optimizing the target function L to obtain presentation content of the vector space data; and obtaining an expression of the evaluation function f(d,r,s) for the drug-disease relevance relation according to the presentation content of the vector space data, wherein the presentation content of the vector space data and the expression of the evaluation function f(d,r,s) for the drug-disease relevance relation constitute the pharmacodynamic relation model.

In some embodiments of the present disclosure, a method for optimizing the target function L is a stochastic gradient descent algorithm.

In some embodiments of the present disclosure, a dimension of the real vector space is k, where k<n and both n and k are less than the number of types of drugs in the drug information and the number of types of diseases in the disease information.

In some embodiments of the present disclosure, the dimension of the real vector space is 300-500.

In some embodiments of the present disclosure, the evaluation function f(d,r,s) for the drug-disease relevance relation comprises an evaluation function f(d,r1,s) for the drug-disease therapeutic relation and/or an evaluation function f(d,r0,s) for the drug-disease side-effect relation, wherein $f(d,r1,s) = \|Mc \times dv - Mc \times sv - vr\|_2$; and $f(d,r0,s) = \|Ms \times dv - Ms \times sv - vs\|_2$.

In some embodiments of the present disclosure, after constructing a pharmacodynamic relation model, the method for analyzing a drug-disease relevance relation further comprises:

receiving drug information;

analyzing the drug information according to the pharmacodynamic relation model to obtain relevance relations between a drug in the drug information and different diseases, wherein the relevance relations between the drug in the drug information and different diseases comprise therapeutic relations between the drug in the drug information and different diseases and/or side-effect relations between the drug in the drug information and different diseases; and outputting the relevance relations between the drug in the drug information and different diseases; or, the method for analyzing a drug-disease relevance relation further comprises:

receiving disease information;

analyzing the disease information according to the pharmacodynamic relation model to obtain relevance relations between different drugs and a disease in the disease information, wherein the relevance relations between different drugs and the disease in the disease information comprise therapeutic relations between different drugs and the disease in the disease information and/or side-effect relations between different drugs and the disease in the disease information; and outputting the relevance relations between different drugs and the disease in the disease information; or, the method for analyzing a drug-disease relevance relation further comprises:

receiving drug information and disease information;

analyzing the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and outputting the relevance relation between the drug in the drug information and the disease in the disease information.

In yet another aspect, some embodiments of the present disclosure provide a non-transitory computer-readable storage medium storing executable instructions that, when executed by a terminal device, cause the terminal device to:

collect drug information, disease information and drug-disease relevance relation information, wherein the drug-disease relevance relation information comprises at least one of drug-disease therapeutic relation information and drug-disease side-effect relation information; and construct a pharmacodynamic relation model based on the drug information, the disease information and the drug-disease relevance relation information, wherein the pharmacodynamic relation model is configured to analyze a drug-disease relevance relation r, and the drug-disease relevance relation comprises at least one of a drug-disease therapeutic relation $r_1$ and a drug-disease side-effect relation $r_0$.

In some embodiments of the present disclosure, the executable instructions further cause the terminal device to:

obtain a relevance score of the drug-disease relevance relation based on the pharmacodynamic relation model, to evaluate the drug-disease relevance relation.

In some embodiments of the present disclosure, the pharmacodynamic relation model comprises an evaluation function f(d,r,s) for the drug-disease relevance relation and vector space data in a real vector space, $f(d,r,s)=\|M_R \times dv - M_R \times sv - vR\|_2$;

the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, where d represents the drug, s represents the disease, $\|.\|2$ represents L2 norm, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation; the n-dimensional column vector vR for the drug-disease relevance relation comprises an n-dimensional column vector vr for the drug-disease therapeutic relation and/or an n-dimensional column vector vs for the drug-disease side-effect relation;

an expression of the k-dimensional column vector dv for the drug, an expression of the k-dimensional column vector sv for the disease, an expression of the n-dimensional column vector vR for the drug-disease relevance relation, an expression of the n×k-dimensional mapping matrix $M_R$ for the drug-disease relevance relation, and an expression of the evaluation function f(d,r,s) for the drug-disease relevance relation are solved by optimizing a target function L;

$$L = \sum_{(di,r,sj) \in T} \sum_{(di',r,sj') \in T'} \max(0, f(di, r, sj) - f(di', r, sj') + \gamma)$$

where, $f(di, r, sj) = \|M_R \times dvi - M_R \times svj - vR\|_2$ $f(di', r, sj') = \|M_R \times dvi' - M_R \times svj' - vR\|_2$ where T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max (a,b) represents an operation of taking a maximum value of a and b, and γ represents a pre-defined margin and γ≥f(di', r,sj')−f(di,r,sj).

In some embodiments of the present disclosure, a method for optimizing the target function L is a stochastic gradient descent algorithm.

In some embodiments of the present disclosure, a dimension of the real vector space is k, where k<n and both n and k are less than the number of types of drugs in the drug information and the number of types of diseases in the disease information.

In some embodiments of the present disclosure, the executable instructions further cause the terminal device to perform operations selected from a group consisting of:

receiving drug information; analyzing the drug information according to the pharmacodynamic relation model to obtain relevance relations between a drug in the drug information and different diseases, wherein the relevance relation between the drug in the drug information and different diseases comprise therapeutic relations between the drug in the drug information and different diseases and/or side-effect relations between the drug in the drug information and different diseases; and outputting the relevance relations between the drug in the drug information and different diseases, receiving disease information; analyzing the disease information according to the pharmacodynamic relation model to obtain relevance relations between different drugs and a disease in the disease information, wherein the relevance relation between different drugs and the disease in the disease information comprise therapeutic relations between different drugs and the disease in the disease information and/or side-effect relations between different drugs and the disease in the disease information; and outputting the relevance relations between different drugs and the disease in the disease information, and receiving drug information and disease information; analyzing the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and outputting the relevance relation between the drug in the drug information and the disease in the disease information.

BRIEF DESCRIPTION OF THE DRAWINGS

The accompanying drawings described herein are used for providing further understanding of the present disclosure and constitute a part of the present disclosure. Illustrative embodiments of the present disclosure and descriptions thereof are used for explaining the present disclosure, but do not constitute inappropriate limitations to the present disclosure. In the drawings.

DETAILED DESCRIPTION

In order to further describe a method and device for analyzing a drug-disease relevance relation, and a non-transitory computer-readable storage medium according to some embodiments of the present disclosure, which will be described below in detail with reference to the accompanying drawings.

The inventor is aware of a drug repositioning method based on comprehensive similarity measures and two-way random walk algorithm. The method includes: constructing a similarity matrix based on similarity calculation and calculating drug similarity and disease similarity according to the similarity matrix, to construct a drug similarity matrix and a disease similarity matrix. Then, the method further includes: modeling a drug-disease relation as a bipartite graph G(V,E) to construct a drug-disease heterogeneous network, and performing drug repositioning on the drug-disease heterogeneous network based on the two-way random walk algorithm to determine a drug-disease therapeutic relation. In the above method, the two-way random walk algorithm is to perform drug repositioning on the drug-disease heterogeneous network. In addition, the bipartite graph G(V,E) is used to represent the drug-disease relation in the drug-disease heterogeneous network, and an edge E(G) in the bipartite graph G(V,E) represents the drug-disease relevance relation. The inventor realizes that this method cannot distinguish the drug-disease therapeutic relation and the drug-disease side-effect relation, so that drugs may not be accurately selected to treat diseases.

Figure 1:
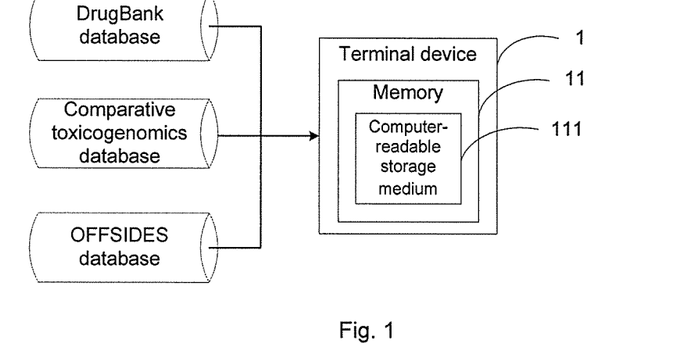
FIG. 1 is a block diagram of a structure of a terminal device according to some embodiments of the present disclosure.

Some embodiments of the present disclosure provide a method for analyzing a drug-disease relevance relation. In some embodiments, the method is executed by a terminal device. The terminal device is, for example, a desktop computer, a notebook computer or a tablet computer. The terminal device is, for example, a server, a server cluster, a cloud computing platform and the like. The terminal device may also be any device with logical operation execution capability In some embodiments, as shown in FIG. 1, the terminal device includes a memory 11, and the memory 11 optionally includes one or more computer-readable storage medium 111. The computer-readable storage medium 111 stores instructions. In some embodiments, the computer-readable storage medium is installed in the terminal device. In some other embodiments, the computer-readable storage medium runs on various computing platforms such as a server and a cloud computing platform.

Figure 2:
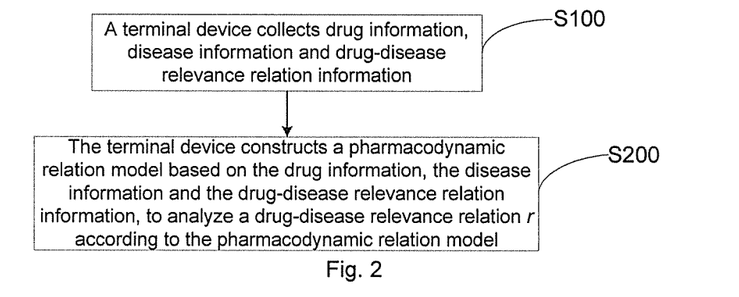
FIG. 2 is a flowchart of a method for analyzing a drug-disease relevance relation according to some embodiments of the present disclosure.

FIG. 2 shows a flowchart of a method for analyzing a drug-disease relevance relation according to some embodiments of the present disclosure. FIG. 2 corresponds to instructions stored in a computer-readable storage medium.

As shown in FIG. 2, the method for analyzing a drug-disease relevance relation according to some embodiments of the present disclosure includes a step 100 and a step 200 (S100 and S200).

In step 100 (S100), a terminal device collects drug information, disease information and drug-disease relevance relation information.

In some embodiments, the terminal device is coupled to various existing medical databases, for example, a DrugBank database, a Comparative Toxicogenomics Database (CTD) and an OFFSIDES database. The DrugBank database stores all drugs approved by a Food and Drug Administration (FDA) which is, for example, food and drug administrations of different nations. The comparative toxicogenomics database stores drug-disease therapeutic relations. The OFFSIDES database stores drug-disease side-effect relations. In some other embodiments, the terminal device is coupled to various cloud platforms storing medical data. Therefore, the terminal device can acquire the drug information, the disease information and the drug-disease relevance relation information stored in the cloud platforms via a network to easily acquire more data.

In some embodiments, the terminal device keeps updating data actively or passively to synchronize with data in the connected databases, so that the drug information, the disease information and the drug-disease relevance relation information are updated constantly.

It will be noted that, in some embodiments, the terminal device is extensible, that is, sources for data collection are expanded according to the appearance of new databases for drug information, disease information and drug-disease relevance relation information.

In some embodiments, as shown in FIG. 1, the terminal device acquires the drug information and the disease information from one or more of the DrugBank database and/or the comparative toxicogenomics database, and the OFF-SIDES database. For example, the terminal device acquires drug-disease therapeutic relation information from the comparative toxicogenomics database. In addition, the terminal device acquires drug-disease side-effect relation information from the OFFSIDES database.

In step 200 (S200), the terminal device constructs a pharmacodynamic relation model based on the drug information, the disease information and the drug-disease relevance relation information, to analyze a drug-disease relevance relation r according to the pharmacodynamic relation model. The drug-disease relevance relation includes a drug-disease therapeutic relation $r_1$ and/or a drug-disease side-effect relation $r_0$.

In the method for analyzing a drug-disease relevance relation according to the embodiments of the present disclosure, existing drug information, disease information and drug-disease relevance relation information are collected by the terminal device to learn the collected existing drug information, disease information and drug-disease relevance relation information and to construct a pharmacodynamic relation model. Since the drug-disease relevance relation information includes drug-disease therapeutic relation information and drug-disease side-effect relation information, the drug-disease relevance relation analyzed by the constructed pharmacodynamic relation model includes a drug-disease therapeutic relation and a drug-disease side-effect relation. Therefore, when the method for analyzing a drug-disease relevance relation is used to treat diseases, a doctor can accurately select drugs, the therapeutic effect of which is good while the side-effect is relatively slight, to treat diseases according to analysis results of the terminal device. And drug researchers can be provided with instructional advice for research on the drug properties.

In some embodiments of the present disclosure, the drug-disease therapeutic relation and the drug-disease side-effect relation are analyzed independently (for example, two pharmacodynamic relation models are constructed simultaneously, so that the analysis on the drug-disease therapeutic relation and the analysis on the drug-disease side-effect relation can be performed independently within the terminal device). In some embodiments of the present disclosure, the drug-disease therapeutic relation and the drug-disease side-effect relation are analyzed simultaneously (the analysis on the drug-disease therapeutic relation and the analysis on the drug-disease side-effect relation are performed simultaneously in a pharmacodynamic relation model). It is easy to understand that, in order to provide medical personnel with comprehensive analysis result outputs, the terminal device can output analysis results for the drug-disease therapeutic relation and the drug-disease side-effect relation simultaneously no matter how the pharmacodynamic relation model is designed.

It can be understood that the process of constructing, by the terminal device, a pharmacodynamic relation model based on the drug information, the disease information and the drug-disease relevance relation information, is actually a representation learning process, that is, the collected drug information, disease information and drug-disease relevance relation information are constructed as a pharmacodynamic relation model by representation learning.

In the medical field, there are several ways to represent the drug-disease relevance relation, for example, by a method for analyzing how drugs and diseases act on human bodies' physiological processes (and the derived mathematically analytical methods, for example, Tanimoto coefficient, Pearson coefficient, etc.). In the embodiments of the present disclosure, a pharmacodynamic relation model is constructed. In some embodiments, the pharmacodynamic relation model includes an evaluation function f(d,r,s) for the drug-disease relevance relation and vector space data in a real vector space, where $f(d,r,s)=\|M_R \times dv - M_R \times sv - vR\|_2$. The vector space data includes a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation.

In the evaluation function, d represents the drug, s represents the disease, and $\|.\|2$ represents L2 norm. Considering that the drug-disease relevance relation information includes drug-disease therapeutic relation information and/or drug-disease side-effect relation information, the n×k-dimensional mapping matrix $M_R$ for the drug-disease relevance relation includes an n×k-dimensional mapping matrix Mc for the drug-disease therapeutic relation and/or an n×k-dimensional mapping matrix Ms for the drug-disease side-effect relation. The n-dimensional column vector vR for the drug-disease relevance relation comprises an n-dimensional column vector vr for the drug-disease therapeutic relation and/or an n-dimensional column vector vs for the drug-disease side-effect relation.

In some embodiments, an expression of the k-dimensional column vector dv for the drug, an expression of the k-dimensional column vector sv for the disease, an expression of the n-dimensional column vector vR for the drug-disease relevance relation, an expression of the n×k-dimensional mapping matrix $M_R$ for the drug-disease relevance relation, and an expression of the evaluation function f(d,r,s) for the drug-disease relevance relation are solved by the following target function L:

$$L = \sum_{(di,r,sj) \in T} \sum_{(di',r,sj') \in T'} \max(0, f(di, r, sj) - f(di', r, sj') + \gamma)$$

where, $$f(di, r, sj) = \|M_R \times dvi - M_R \times svj - vR\|_2$$

$$f(di', r, sj') = \|M_R \times dvi' - M_R \times svj' - vR\|_2$$

where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max (a,b) represents an operation of taking the maximum value of a and b, and γ represents a pre-defined margin. γ≥f(di',r, sj')−f(di,r,sj), that is, a score of drug-disease with relevance is at most γ less than a score of drug-disease without relevance.

In some embodiments of the present disclosure, other types of evaluation functions and target functions are constructed. For example, an indirect score of the relation between a drug and a disease is constructed based on the influence of the drug and the disease on human bodies' physiological processes, and the following evaluation function S is constructed by Tanimoto coefficient p ($p_{drug,k}$ represents a physiological process effect caused by the act of a drug on human bodies and $p_{disease,k}$ represents a physiological process effect caused by the act of the disease on human bodies): $S_{drug,disease\ i} = -\lg \Sigma \sqrt{p_{drug,k} \times p_{diseasei,k}}$. In some other embodiments of the present disclosure, the evaluation function S is combined with the target function L according to embodiments of the present disclosure.

In the evaluation function according to the embodiments of the present disclosure, the known drug-disease relevance relation information in the public databases is used fully and L2 norm is constructed. The pertinence, the accuracy and the efficiency of the evaluation function are improved.

Figure 3:
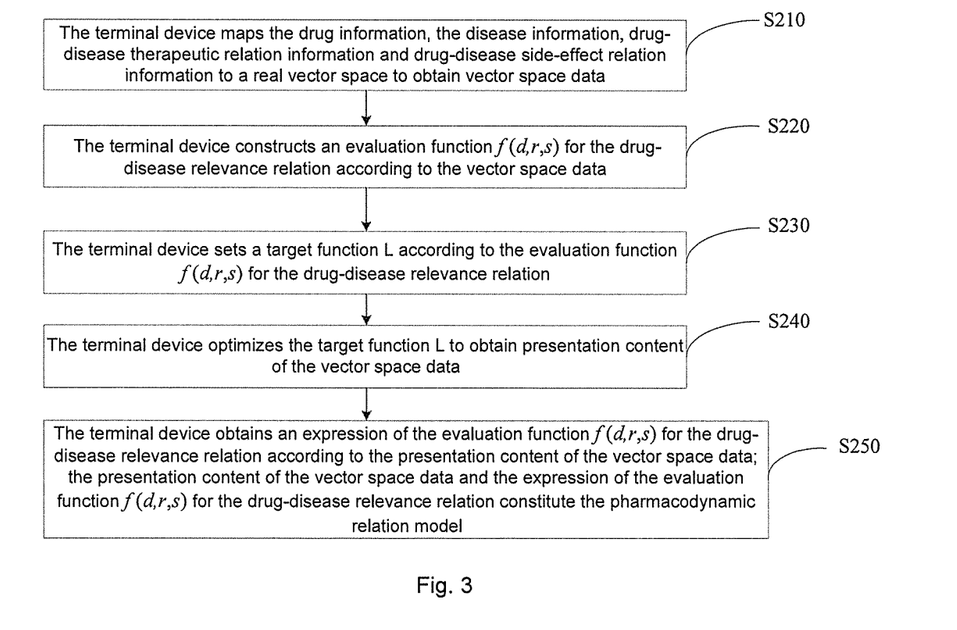
FIG. 3 is a flowchart of a method for constructing a pharmacodynamic relation model according to some embodiments of the present disclosure.

Next, referring to FIG. 3, FIG. 3 shows a flowchart of a method for constructing a pharmacodynamic relation model according to some embodiments of the present disclosure. In some embodiments of the disclosure, the method is executed by a terminal device. FIG. 3 corresponds to instructions stored in a computer-readable storage medium.

As shown in FIG. 3, the method for constructing a pharmacodynamic relation model based on drug information, disease information and drug-disease relevance relation information includes steps 210-250 (S210-S250).

In step 210 (S210), the terminal device maps the drug information, the disease information, drug-disease therapeutic relation information and drug-disease side-effect relation information to a real vector space to obtain vector space data. The vector space data includes a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation. The n-dimensional column vector vR for the drug-disease relevance relation comprises an n-dimensional column vector vr for the drug-disease therapeutic relation and/or an n-dimensional column vector vs for the drug-disease side-effect relation. The n×k-dimensional mapping matrix $M_R$ for the drug-disease relevance relation includes an n×k-dimensional mapping matrix Mc for the drug-disease therapeutic relation and/or an n×k-dimensional mapping matrix Ms for the drug-disease side-effect relation.

In step 220 (S220), the terminal device constructs an evaluation function f(d,r,s) for the drug-disease relevance relation according to the vector space data.

For example, the evaluation function f(d,r,s) for the drug-disease relevance relation includes an evaluation function f(d,r1,s) for the drug-disease therapeutic relation and an evaluation function f(d,r0,s) for the drug-disease side-effect relation:

$$f(d,r1,s) = \|Mc \times dv - Mc \times sv - vr\|_2$$

$$f(d,r0,s) = \|Ms \times dv - Ms \times sv - vs\|_2$$

Where, in constructing the evaluation function f(d,r,s) for the drug-disease relevance relation, assumed that there is a relevance relation (a therapeutic relation and/or a side-effect relation) between a drug d and a disease s, after the k-dimensional column vector dv for the drug and the k-dimensional column vector sv for the disease are mapped to a space, in which the n-dimensional column vector vR for the drug-disease relevance relation (the n-dimensional column vector vr for the drug-disease therapeutic relation and the n-dimensional column vector vs for the drug-disease side-effect relation) is located, by the n×k-dimensional mapping matrix $M_R$ for the drug-disease relevance relation (the n×k-dimensional mapping matrix Mc for the drug-disease therapeutic relation and the n×k-dimensional mapping matrix Ms for the drug-disease side-effect relation), $M_R \times dv - M_R \times sv \approx vR$ (Mc×dv−Mc×sv≈vr or Ms×dv−Ms×sv≈vs). That is, the possibility that there is a relevance relation between the drug d and the disease s is higher if the value of $M_R \times dv - M_R \times sv - vR$ is smaller.

In step 230 (S230), the terminal device sets a target function L according to the evaluation function f(d,r,s) for the drug-disease relevance relation.

For example, the target function L includes a target function Lr1 for the drug-disease therapeutic relation and a target function Lr0 for the drug-disease side-effect relation Lr0:

$$Lr1 = \sum_{(di,r1,sj) \in T} \sum_{(di',r1,sj') \in T'} \max(0, f(di, r1, sj) - f(di', r1, sj') + \gamma)$$

$$Lr0 = \sum_{(di,r0,sj) \in T} \sum_{(di',r0,sj') \in T'} \max(0, f(di, r0, sj) - f(di', r0, sj') + \gamma)$$

In step 240 (S240), the terminal device optimizes the target function L to obtain presentation content of the vector space data. In some embodiments, the presentation content of the vector space data includes: an expression of the k-dimensional column vector dv for the drug, an expression of the k-dimensional column vector sv for the disease, an expression of the n-dimensional column vector vR for the drug-disease relevance relation, and an expression of the n×k-dimensional mapping matrix $M_R$ for the drug-disease relevance relation. Optimizing the target function L is actually to minimize the target function, so that the solved expression is optimal and meets the requirement on a pre-defined margin γ.

In some embodiments, a method for optimizing the target function L is a stochastic gradient descent algorithm. When the target function L is optimized by the stochastic gradient descent algorithm, an iterative updating can be performed once by each sample. If the sample size is very large (for example, there are hundreds of thousands of samples), then the target function may be optimized by just tens of thousands or thousands of samples. In some other embodiments, as the method for optimizing the target function L, other optimization methods with a minimizing function can be used.

In step 250 (S250), the terminal device obtains an expression of the evaluation function f(d,r,s) for the drug-disease relevance relation according to the presentation content of the vector space data. The presentation content of the vector space data and the expression of the evaluation function f(d,r,s) for the drug-disease relevance relation constitute the pharmacodynamic relation model.

By the above analysis, it can be found that, after minimizing the target function L by introducing the requirement on a pre-defined margin γ in the target function L and limiting γ≥f(di',r,sj')−f(di,r,sj), a score of drug-disease with relevance is at most γ less than a score of drug-disease without relevance in the obtained expression.

In some embodiments, the expression of the evaluation function for the drug-disease relevance relation includes an expression of the evaluation function for the drug-disease therapeutic relation and an expression of the evaluation function for the drug-disease side-effect relation. Known from the expression of the evaluation function for the drug-disease therapeutic relation and the expression of the evaluation function for the drug-disease side-effect relation, the evaluation function for the drug-disease relevance relation is just in one-to-one correspondence with one drug d, one disease s and the drug-disease relevance relation. Therefore, when the relevance relations between a certain drug and different diseases are analyzed, the relevance relations between the drug and different diseases can be analyzed in parallel, and do not need to be performed in turn. Similarly, when the relevance relations between different drugs and a certain disease are analyzed, the relevance relations between different drugs and the disease can be analyzed in parallel, and do not need to be performed in turn. Therefore, by the expression of the evaluation function for the drug-disease relevance relation according to the embodiments of the present disclosure, the analysis speed for drugs can be greatly increased and then the data analysis efficiency is improved.

The method for analyzing a drug-disease relevance relation according to embodiments of the present disclosure will be described below by examples.

The terminal device collects a drug and a disease, which have a therapeutic relation therebetween, from the CTD, for example, antiviral capsule and viral cold, and collects a drug and a disease, which have a side-effect relation therebetween, from the OFFSIDES database, for example, ephedrine and agrypnia. That is, the collected drug information is antiviral capsule and ephedrine, and the disease information is viral cold and agrypnia. The drug-disease therapeutic relation information includes the therapeutic relation between viral cold and antiviral capsule, and the drug-disease side-effect relation information includes the side-effect relation between ephedrine and agrypnia.

The collected drug information, disease information, drug-disease therapeutic relation information and drug-disease side-effect relation information constitute a set T with relevance. Also, since the sources of these data are databases recognized by the existing medical field, it is considered that these data is correct information (for example, antiviral capsules can treat viral cold) and there is not wrong information (for example, stones can treat viral cold). Therefore, generally speaking, these data collected from the existing databases or cloud platforms may not constitute a set T' without relevance. In some examples, in constructing the target function L by the terminal device, consumed that a set T' without relevance is constructed by the following method.

First, a triple of a drug, a disease and a drug-disease relevance relation is randomly extracted from the set T with relevance and set as (di,r,sj). Then, assumed that the drug di is constant, a disease is randomly extracted from the existing medical databases. Since it cannot be determined whether there is a relevance relation between the drug di and the randomly-extracted disease, assumed that there is no correspondence between the drug di and the randomly-extracted disease, a triple without relevance can be constituted by the drug di, the randomly-extracted disease and the correspondence therebetween. The triple without relevance is represented by (di',r,sj'), and is considered as an element of the set T' without relevance.

Then, another triple of a drug, a disease and a drug-disease relevance relation is randomly extracted from the set T with relevance and another triple (di',r,sj') without relevance is constructed by the above method. Similarly, the construction of the set T' without relevance is finished.

It will be noted that, in general, there are just several diseases which each drug can treat, but there are up to hundreds of thousands of diseases in the medical databases, so that there is basically no relevance relation between drugs and diseases in the triples extracted by this random method. For example, assumed that each drug treats 10 diseases and there are 100 thousand diseases in the databases, triples extracted by the above random method belong to the set T' without relevance with a possibility of (1−10/100000)=99.99%.

In view of massive medical data, the data sparsity of medical data is high. In general, a similarity matrix is constructed based on similarity calculation, and the drug-disease relevance relation is modeled as a bipartite graph G(V,E) to represent the drug-disease relevance relation with the bipartite graph and construct a drug-disease heterogeneous network. The drug-disease heterogeneous network is actually constructed by the relevance analysis method. This cannot solve the problem of data sparsity. In some embodiments of the present disclosure, the dimension of the real vector space is 300-500. In this way, the dimension of the real vector space is low, and data of the drug information, the disease information, the drug-disease therapeutic relation information and the drug-disease side-effect relation information can be mapped to a real vector space with low dimension, so that the original data with high sparsity becomes data with low sparsity. In doing so, when data is processed, data processing can be performed in a space with low dimension, so that the method for analyzing a drug-disease relevance relation can greatly process medical data with high data sparsity.

In some embodiments, k<n, where both n and k are less than the number of types of drugs in the drug information and the number of types of diseases in the disease information. In some embodiments, in order to ensure that the dimension of the real vector space is 300-500, k and n are selected in advance, and the range of the set value for k and n is within 300-500 and k<n. And in this case, the number of types of drugs in the drug information and the number of types of diseases in the disease information are greater than 500. Such a setting makes sense. In other words, when both n and k are less than the number of types of drugs in the drug information and the number of types of diseases in the disease information, after a pharmacodynamic relation model is constructed based on the drug information and the disease information, the dimension can be reduced to solve the problem of data sparsity, the detailed analysis of which refers to the foregoing description.

Figure 4:
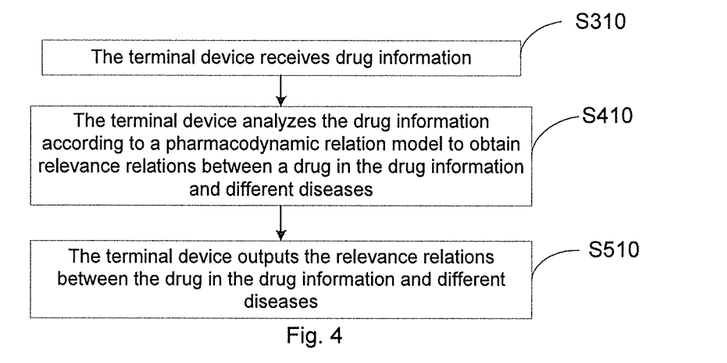
FIG. 4 is a flowchart of a method included in a method for analyzing a drug-disease relevance relation after constructing a pharmacodynamic relation model according to some embodiments of the present disclosure.

Referring to FIG. 4 below, FIG. 4 shows a flowchart of a method included in a method for analyzing a drug-disease relevance relation after constructing a pharmacodynamic relation model according to some embodiments of the present disclosure. The method included is proposed in consideration of the need to analyze a relevance relation between a certain drug and different diseases. In some embodiments, the method included is executed by a terminal device. FIG. 4 corresponds to instructions stored in a computer-readable storage medium.

As shown in FIG. 4, the method included in a method for analyzing a drug-disease relevance relation after constructing a pharmacodynamic relation model includes steps 310-510 (S310-S510).

In step 310 (S310), the terminal device receives drug information.

In step 410 (S410), the terminal device analyzes the drug information according to a pharmacodynamic relation model to obtain relevance relations between a drug in the drug information and different diseases.

In step 510 (S510), the terminal device outputs the relevance relations between the drug in the drug information and different diseases.

In some embodiments, in order to provide effective outputs, the terminal device obtains a relevance score of the drug-disease relevance relation based on the pharmacodynamic relation model, and evaluates the drug-disease relevance relation (significance evaluation) based on the relevance score. It is easy to understand that a lower score indicates that the drug-disease relevance relation has higher significance. In some embodiments, the terminal device screens drug-disease relevance relations which have significance based on a ranking result of relevance scores of the drug-disease relevance relations.

In some embodiments, significance is evaluated by presetting a score threshold. The significance is determined by judging whether a score is or not higher than the threshold. In some other embodiments, statistical analysis is performed on lots of pharmacodynamic relations based on the pharmacodynamic relation model according to the embodiments of the present disclosure. The score range which has significance, obtained by the statistical analysis, is considered as an instructional score range, which is considered as the significance evaluation criterion. In still other embodiments, the score range which has significance is obtained by some test methods in statistical mathematics, for example, a Z-score method (that is, output results of the evaluation function are normalized and ranked, so that random errors are restrained).

Figure 5:
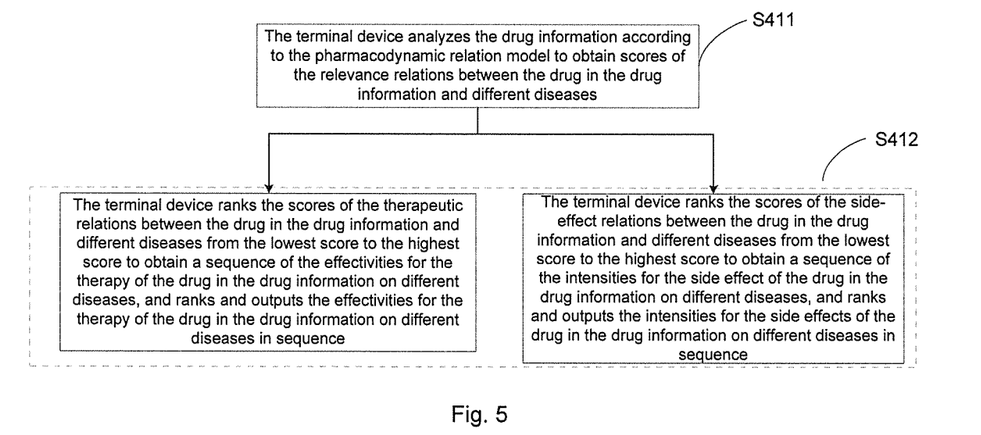
FIG. 5 is a flowchart of a method for analyzing drug information according to a pharmacodynamic relation model to obtain a relevance relation between a drug in drug information and different diseases according to some embodiments of the present disclosure.

Referring to FIG. 5 below, FIG. 5 shows a flowchart of a method for analyzing drug information according to a pharmacodynamic relation model to obtain relevance relations between a drug in the drug information and different diseases according to some embodiments of the present disclosure. In some embodiments, the method is executed by a terminal device. FIG. 5 corresponds to instructions in a computer-readable storage medium.

As shown in FIG. 5, the method for analyzing drug information according to a pharmacodynamic relation model to obtain relevance relations between a drug in the drug information and different diseases includes a step 411 and a step 412 (S411 and S412).

In step 411 (S411), the terminal device analyzes the drug information according to the pharmacodynamic relation model to obtain scores of the relevance relations between a drug in the drug information and different diseases. In some embodiments, the scores of the relevance relations between the drug in the drug information and different diseases include scores of therapeutic relations between the drug in the drug information and different diseases, and scores of side-effect relations between the drug in the drug information and different diseases.

In step 412 (S412), the terminal device ranks the scores of the therapeutic relations between the drug in the drug information and different diseases from the lowest score to the highest score to obtain a sequence of the effectivities for the therapy of the drug in the drug information on different diseases, and ranks and outputs the effectivities for the therapy of the drug in the drug information on different diseases in sequence. A lower score of the therapeutic relation between the drug in the drug information and a disease indicates a higher effectivity for the therapy of the drug in the drug information on the disease.

Also, the terminal device ranks the scores of the side-effect relations between the drug in the drug information and different diseases from the lowest score to the highest score to obtain a sequence of the intensities for the side effect of the drug in the drug information on different diseases, and ranks and outputs the intensities for the side effect of the drug in the drug information on different diseases in sequence. A lower score of the side-effect relation between the drug in the drug information and a disease indicates a higher side effect of the drug in the drug information on the disease.

Figure 6:
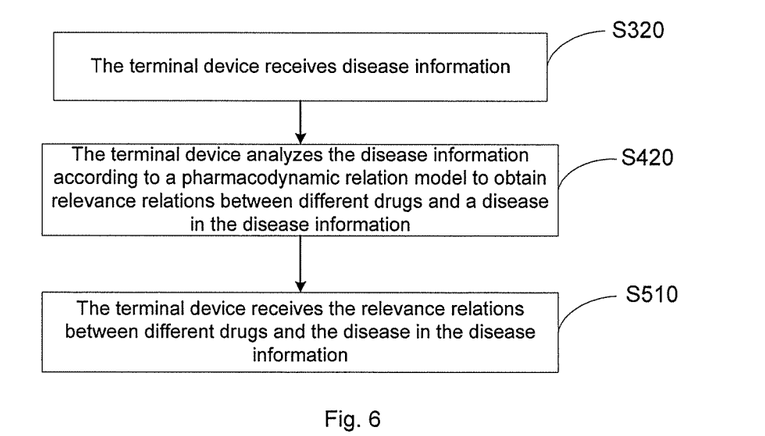
FIG. 6 is a flowchart of another method included in a method for analyzing a drug-disease relevance relation after constructing a pharmacodynamic relation model according to some embodiments of the present disclosure.

Referring to FIG. 6 below, FIG. 6 shows a flowchart of another method included in a method for analyzing a drug-disease relevance relation after constructing a pharmacodynamic relation model according to some embodiments of the present disclosure. The method included is proposed in consideration of the need to analyze relevance relations between different drugs and a certain disease. In some embodiments, the method included is executed by a terminal device. FIG. 6 corresponds to instructions stored in a computer-readable storage medium.

As shown in FIG. 6, the method included in a method for analyzing a drug-disease relevance relation after constructing a pharmacodynamic relation model includes steps 320-520 (S320-S520).

In step 320 (S320), the terminal device receives disease information.

In step 420 (S420), the terminal device analyzes the disease information according to a pharmacodynamic relation model to obtain relevance relations between different drugs and a disease in the disease information. In some embodiments, the relevance relations between different drugs and the disease in the disease information include therapeutic relations between different drugs and the disease in the disease information, and side-effect relations between different drugs and the disease in the disease information.

In step 520 (S520), the terminal device outputs the relevance relations between different drugs and the disease in the disease information.

Figure 7:
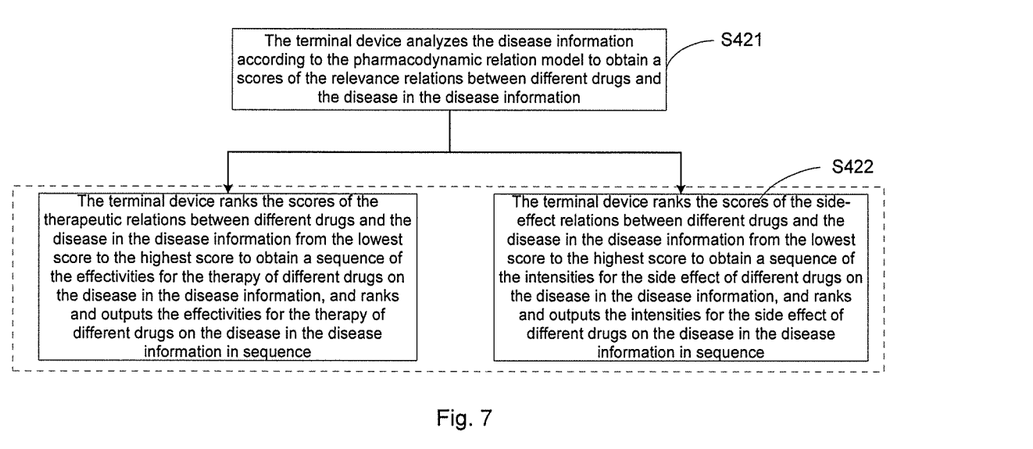
FIG. 7 is a flowchart of a method for analyzing disease information according to a pharmacodynamic relation model to obtain a relevance relation between different drugs and a disease in disease information according to some embodiments of the present disclosure.

Referring to FIG. 7 below, FIG. 7 shows a flowchart of a method for analyzing disease information according to a pharmacodynamic relation model to obtain relevance relations between different drugs and a disease in the disease information according to some embodiments of the present disclosure. In some embodiments, the method is executed by a terminal device. FIG. 7 corresponds to instructions in a computer-readable storage medium.

As shown in FIG. 7, the method for analyzing disease information according to a pharmacodynamic relation model to obtain relevance relations between different drugs and a disease in the disease information includes a step 421 and a step 422 (S421 and S422).

In step 421 (S421), the terminal device analyzes the disease information according to the pharmacodynamic relation model to obtain scores of the relevance relations between different drugs and a disease in the disease information. In some embodiments, the scores of the relevance relations between different drugs and the disease in the disease information include scores of therapeutic relations between different drugs and the disease in the disease information, and scores of side-effect relations between different drugs and the disease in the disease information.

In step 422 (S422), the terminal device ranks the scores of the therapeutic relations between different drugs and the disease in the disease information from the lowest score to the highest score to obtain a sequence of the effectivities for the therapy of different drugs on the disease in the disease information, and ranks and outputs the effectivities for the therapy of different drugs on the disease in the disease information in sequence. A lower score of the therapeutic relation between a drug and the disease in the disease information indicates a higher effectivity for the therapy of the drug on the disease in the disease information.

In addition, the terminal device ranks the scores of the side-effect relations between different drugs and the disease in the disease information from the lowest score to the highest score to obtain a sequence of the intensities for the side effect of different drugs on the disease in the disease information, and ranks and outputs the intensities for the side effect of different drugs on the disease in the disease information in sequence. A lower score of the side-effect relation between a drug and the disease in the disease information indicates a higher side effect of the drugs on the disease in the disease information.

Figure 8:
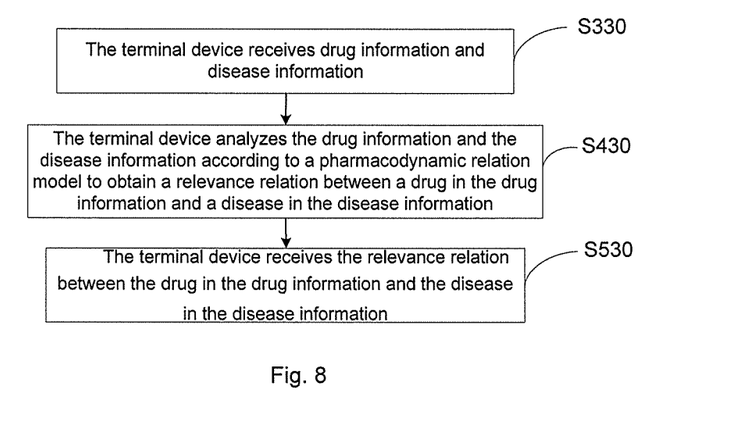
FIG. 8 is a flowchart of a still other method included in a method for analyzing a drug-disease relevance relation after constructing a pharmacodynamic relation model according to some embodiments of the present disclosure.

Referring to FIG. 8 below, FIG. 8 shows a flowchart of a still other method included in a method for analyzing a drug-disease relevance relation after constructing a pharmacodynamic relation model according to some embodiments of the present disclosure. The included method is proposed in consideration of the need to analyze a relevance relation between a certain drug and a certain disease. In some embodiments, the method included is executed by a terminal device. FIG. 8 corresponds to instructions stored in a computer-readable storage medium.

As shown in FIG. 8, the method included in a method for analyzing a drug-disease relevance relation after constructing a pharmacodynamic relation model includes steps 330-530 (S330-S530).

In step 330 (S330), the terminal device receives drug information and disease information.

In step 430 (S430), the terminal device analyzes the drug information and the disease information according to a pharmacodynamic relation model to obtain a relevance relation between a drug in the drug information and a disease in the disease information. In some embodiments, the relevance relation between the drug in the drug information and the disease in the disease information includes a therapeutic relation between the drug in the drug information and the disease in the disease information and a side-effect relation between the drug in the drug information and the disease in the disease information.

In the step 530 (S530), the terminal device outputs the relevance relation between the drug in the drug information and the disease in the disease information.

Figure 9:
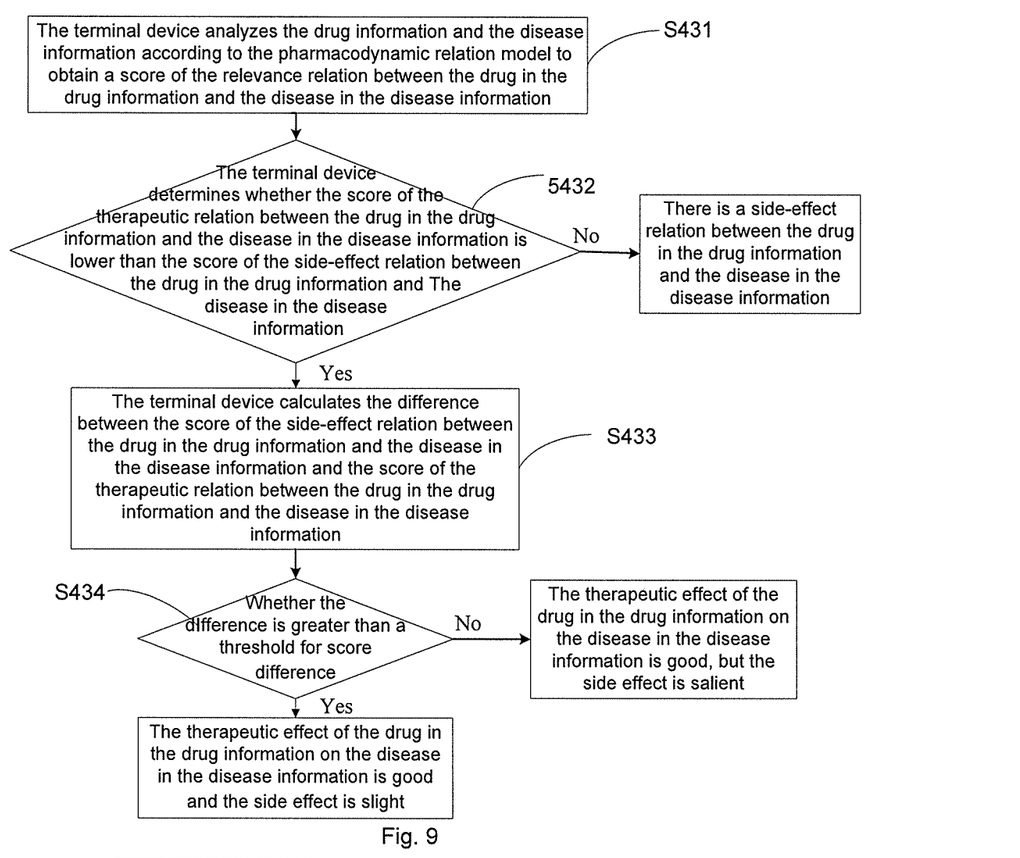
FIG. 9 is a flowchart of a method for analyzing drug information and disease information according to a pharmacodynamic relation model to obtain a relevance relation between a drug in drug information and a disease the disease information according to some embodiments of the present disclosure.

Referring to FIG. 9 below, FIG. 9 shows a flowchart of a method for analyzing drug information and disease information according to a pharmacodynamic relation model to obtain a relevance relation between a drug in the drug information and a disease in the disease information according to some embodiments of the present disclosure. In some embodiments, the method is executed by a terminal device. FIG. 9 corresponds to instructions in a computer-readable storage medium.

As shown in FIG. 9, the method for analyzing drug information and disease information according to a pharmacodynamic relation model to obtain a relevance relation between a drug in the drug information and a disease in the disease information includes a step 431 and a step 432 (S431 and S432).

In step 431 (S431), the terminal device analyzes the drug information and the disease information according to the pharmacodynamic relation model to obtain a score of the relevance relation between a drug in the drug information and a disease in the disease information. In some embodiments, the score of the relevance relation between the drug in the drug information and the disease in the disease information includes a score of a therapeutic relation between the drug in the drug information and the disease in the disease information and a score of a side-effect relation between the drug in the drug information and the disease in the disease information.

In step 432 (S432), the terminal device determines whether the score of the therapeutic relation between the drug in the drug information and the disease in the disease information is less than the score of the side-effect relation between the drug in the drug information and the disease in the disease information. If so, the therapeutic effect of the drug in the drug information on the disease in the disease information is relatively obvious and there is a therapeutic relation between the drug in the drug information and the disease in the disease information. It is considered to use the drug in the drug information to treat the disease in the disease information, and the S433 is executed. Otherwise, the side effect of the drug in the drug information on the disease in the disease information is relatively obvious and there is a side-effect relation between the drug in the drug information and the disease in the disease information. Therefore, the drug in the drug information cannot be used to treat the disease in the disease information.

In step 433 (S433), the terminal device calculates the difference between the score of the side-effect relation between the drug in the drug information and the disease in the disease information and the score of the therapeutic relation between the drug in the drug information and the disease in the disease information. Greater difference indicates that the side effect is slighter when the drug in the drug information is selected to treat the disease in the disease information. The specific difference is determined by a person who gives drugs and will not be limited in the embodiments of the present disclosure.

In step 434 (S434), the terminal device determines whether the difference is greater than a threshold for score difference. If so, the therapeutic effect of the drug in the drug information on the disease in the disease information is good and the side effect is slight, so that the drug is selected to treat the disease. Otherwise, if the therapeutic effect of the drug in the drug information on the disease in the disease information is good, but the side effect is salient, the drug is not used to treat the disease.

It will be noted that, if the score of the therapeutic relation between the drug in the drug information and the disease in the disease information is lower than the score of the side-effect relation between the drug in the drug information and the disease in the disease information, or the score of the therapeutic relation between the drug in the drug information and the disease in the disease information is too high, the drug in the drug information cannot be selected to treat the disease in the disease information. This is because that, a higher score of the therapeutic relation between the drug in the drug information and the disease in the disease information indicates worse therapeutic effect of the drug in the drug information on the disease in the disease information. Therefore, in some embodiments of the present disclosure, when the score of the therapeutic relation between the drug in the drug information and the disease in the disease information is lower than the score of the side-effect relation between the drug in the drug information and the disease in the disease information, it is determined whether the score of the therapeutic relation between the drug in the drug information and the disease in the disease information is lower than the minimum score threshold. If so, the S433 may be executed; or otherwise, the drug is not used.

Figure 10:
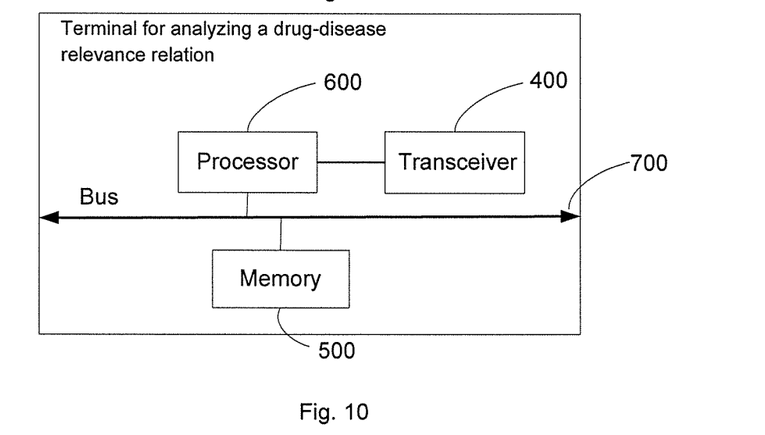
FIG. 10 is a schematic structure diagram of a terminal for analyzing a drug-disease relevance relation according to some embodiments of the present disclosure.

As shown in FIG. 10, some embodiments of the present disclosure provide a terminal for analyzing a drug-disease relevance relation, including a transceiver 400 and a processor 600. In some embodiments, the terminal further includes a memory 500. The transceiver 400, the memory 500 and the processor 600 communicate with each other via a bus 700. In some embodiments, the terminal for analyzing a drug-disease relevance relation includes the terminal device according to the above embodiments.

The transceiver 400 is configured to support an communication between the processor 600 and an external database, so that the processor 600 collects drug information, disease information and drug-disease relevance relation information; and also to support an communication between the processor 600 and an external display device, so that analysis results of the processor 600 are displayed through the display device.

The memory 500 is configured to store application programs designed for executing the method for analyzing a drug-disease relevance relation. The processor 600 is configured to load the application programs to execute the method for analyzing a drug-disease relevance relation.

In some embodiments, the processor 600 refers to one processor. In other embodiments, the processor 600 is a collective term of multiple processing elements. For example, the processor 600 is a Central Processing Unit (CPU), an Application Specific Integrated Circuit (ASIC), or one or more integrated circuits, for example, one or more Digital Signal Processors (DSPs), or one or more Field Programmable Gate Arrays (FPGAs).

In some embodiments, the memory 500 is a storage device. In other embodiments, the memory 500 is a collective term of multiple storage elements and is configured to store executable programs codes or the like. In some embodiments, the memory 500 includes Random Access Memory (RAM), non-volatile memory, for example, magnetic disk memory, flash, etc.

The bus 700 is, for example, an Industry Standard Architecture (ISA) bus, a Peripheral Component (PCI) bus or an Extended Industry Standard Architecture (EISA) bus, etc. The bus 700 includes, for example, an address bus, a data bus, a control bus or the like. For convenience of expression, the bus is expressed by only one bold line in FIG. 10, but it does not mean that there is only one bus or one type of buses.

In some embodiments of the present disclosure, the transceiver 400 is configured to receive drug information, disease information and drug-disease relevance relation information. The drug-disease relevance relation information includes drug-disease therapeutic relation information and/or drug-disease side-effect relation information. The processor 600 is configured to construct a pharmacodynamic relation model based on the drug information, the disease information and the drug-disease relevance relation information. The pharmacodynamic relation model is used to analyze a drug-disease relevance relation r. The drug-disease relevance relation includes a drug-disease therapeutic relation $r_1$ and/or a drug-disease side-effect relation $r_0$.

Beneficial effects of the terminal for analyzing a drug-disease relevance relation according to the embodiments of the present disclosure is the same as the beneficial effects of the method for analyzing a drug-disease relevance relation according to the above embodiments and will not be repeated here.

In some embodiments, the processor 600 is configured to map the drug information, the disease information and the drug-disease relevance relation information to a real vector space to obtain vector space data. The vector space data includes entity space data, relation space data and space conversion data which realizes the conversion between the entity space data and the relation space data. The entity space data includes a k-dimensional column vector dv for a drug and a k-dimensional column vector sv for a disease, and the relation space data includes an n-dimensional column vector vR for the drug-disease relevance relation. The n-dimensional column vector vR for the drug-disease relevance relation includes an n-dimensional column vector vr for the drug-disease therapeutic relation and/or an n-dimensional column vector vs for the drug-disease side-effect relation. The space conversion data includes an n×k-dimensional mapping matrix $M_R$ for the drug-disease relevance relation, and the n×k-dimensional mapping matrix $M_R$ for the drug-disease relevance relation includes an n×k-dimensional mapping matrix Mc for the drug-disease therapeutic relation and/or an n×k-dimensional mapping matrix Ms for the drug-disease side-effect relation.

In some embodiments, the dimension of the real vector space is 300-500, where k<n and both n and k are less than the number of types of drugs in the drug information and the number of types of diseases in the disease information.

In some embodiments, the processor 600 is configured to construct an evaluation function f(d,r,s) for the drug-disease relevance relation according to the vector space data, and $f(d,r,s)=\|M_R \times dv - M_R \times sv - vR\|_2$, where d represents a drug, s represents a disease, and $\|.\|2$ represents L2 norm.

For example, the evaluation function f(d,r,s) for the drug-disease relevance relation includes an evaluation function f(d,r1,s) for the drug-disease therapeutic relation and an evaluation function f(d,r0,s) for the drug-disease side-effect relation;

$$f(d,r1,s)=\|Mc \times dv - Mc \times sv - vr\|_2;$$

$$f(d,r0,s)=\|Ms \times dv - Ms \times sv - vs\|_2;$$

The processor 600 is further configured to set a target function L according to the evaluation function f(d,r,s) for the drug-disease relevance relation;

$$L = \sum_{(di,r,sj) \in T} \sum_{(di',r,sj') \in T'} \max(0, f(di, r, sj) - f(di', r, sj') + \gamma)$$

where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max (a,b) represents an operation of taking a maximum value of a and b, and γ represents a pre-defined margin and γ≥f(di', r,sj')−f(di,r,sj);

In some embodiments, the processor 600 is further configured to optimize the target function L to obtain presentation content of the vector space data. Virtually, the optimization method is to minimize the target function. As the method for optimizing the target function L, a stochastic gradient descent algorithm may be selected, and other optimization methods with minimizing process are possible.

In some embodiments, the processor 600 is configured to obtain an expression of the evaluation function f(d,r,s) for the drug-disease relevance relation according to the presentation content of the vector space data. The presentation content of the vector space data and the expression of the evaluation function f(d,r,s) for the drug-disease relevance relation constitute the pharmacodynamic relation model.

In consideration of the need to analyze relevance relations between a certain drug and different diseases, after constructing a pharmacodynamic relation model, the processor 600 is further configured to receive drug information and analyze the drug information according to the pharmacodynamic relation model to obtain relevance relations between the drug in the drug information and different diseases. The specific process refers to the foregoing description. In some examples, the relevance relations between the drug in the drug information and different diseases include therapeutic relations between the drug in the drug information and different diseases, and side-effect relations between the drug in the drug information and different diseases. In addition, the transceiver 400 is further configured to output the relevance relations between the drug in the drug information and different diseases.

In consideration of the need to analyze relevance relations between different drugs and a certain disease, in other embodiments, after constructing a pharmacodynamic relation model, the processor 600 is configured to receive disease information and analyze the disease information according to the pharmacodynamic relation model to obtain relevance relations between different drugs and a disease in the disease information. The specific process refers to the foregoing description. In some examples, the relevance relations between different drugs and the disease in the disease information include therapeutic relations between different drugs and the disease in the disease information, and side-effect relations between different drugs and the disease in the disease information. In addition, the transceiver 400 is further configured to output the relevance relations between different drugs and the disease in the disease information.

In consideration of the need to analyze a relevance relation between a certain drug and a certain disease, in still other embodiments, after constructing a pharmacodynamic relation model, the processor 600 is further configured to receive drug information and disease information, and analyze the drug information and the disease information according to the pharmacodynamic relation model to obtain a relevance relation between a drug in the drug information and a disease in the disease information. The specific process refers to the foregoing description. In some examples, the relevance relation between the drug in the drug information and the disease in the disease information includes a therapeutic relation between the drug in the drug information and the disease in the disease information and a side-effect relation between the drug in the drug information and the disease in the disease information. In addition, the transceiver 400 is further configured to output the relevance relation between the drug in the drug information and the disease in the disease information.

The embodiments of the present invention have been described progressively, the identical or similar portions of the embodiments can refer to each other, and each embodiment focuses on the difference from other embodiments. Particularly, for the device embodiments, since these embodiments are basically similar to the method embodiments, the device embodiments have been described simply, and the related description can refer to the description of the method embodiments.

It may be understood by a person of ordinary skill in the art that all or part of the flows in the method embodiments may be implemented by instructing related hardware using computer programs, and the programs may be stored in a computer readable storage medium, and when executed, may include the flows of the embodiments of the methods. Wherein, the storage medium may be a magnetic disk, an optical disk, an ROM (Read-Only Memory), an RAM (Random Access Memory) or the like.

The foregoing descriptions merely show specific implementations of the present disclosure, and the protection scope of the present disclosure is not limited thereto. A person of ordinary skill in the art can readily conceive of variations or replacements within the technical scope disclosed by the embodiments of the present disclosure, and these variations or replacements shall fall into the protection scope of the present disclosure. Accordingly, the protection scope of the present disclosure shall be subject to the protection scope defined by the claims.

What is claimed is:

1. A terminal for analyzing a drug-disease relevance relation, comprising:
   a transceiver, configured to receive drug information, disease information and drug-disease relevance relation information, wherein the drug-disease relevance relation information comprises at least one of drug-disease therapeutic relation information and drug-disease side-effect relation information; and
   a processor, coupled with the transceiver and configured to construct a pharmacodynamic relation model based on the drug information, the disease information and the drug-disease relevance relation information, wherein
   the pharmacodynamic relation model is configured to analyze a drug-disease relevance relation r, and the drug-disease relevance relation comprises at least one of a drug-disease therapeutic relation $r_1$ and a drug-disease side-effect relation $r_0$, wherein
   the transceiver and the processor are configured to be selected from a group consisting of:
   the transceiver is configured to receive drug information; the processor is configured to analyze the drug information according to the pharmacodynamic relation model to obtain relevance relations between a drug in the drug information and different diseases, wherein the relevance relations between the drug in the drug information and different diseases comprise therapeutic relations between the drug in the drug information and different diseases and/or side-effect relations between the drug in the drug information and different diseases; and the transceiver is configured to output the relevance relations between the drug in the drug information and different diseases,
   the transceiver is configured to receive disease information; the processor is configured to analyze the disease information according to the pharmacodynamic relation model to obtain relevance relations between different drugs and a disease in the disease information, wherein the relevance relations between different drugs and the disease in the disease information comprise therapeutic relations between different drugs and the disease in the disease information and/or side-effect relations between different drugs and the disease in the disease information; and the transceiver is configured to output the relevance relations between different drugs and the disease in the disease information, and the transceiver is configured to receive drug information and disease information; the processor is configured to analyze the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and the transceiver is configured to output the relevance relation between the drug in the drug information and the disease in the disease information, the pharmacodynamic relation model comprises an evaluation function f(d,r,s) for the drug-disease relevance relation and vector space data in a real vector space, $f(d,r,s)=\|M_R \times dv - M_R \times sv - vR\|_2$;

the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, where d represents the drug, s represents the disease, $\|.\|2$ represents L2 norm, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation; the n-dimensional column vector vR for the drug-disease relevance relation comprises an n-dimensional column vector vr for the drug-disease therapeutic relation and/or an n-dimensional column vector vs for the drug-disease side-effect relation, and wherein the pharmacodynamic relation is configured to provide recommendation with a relevance score of the drug-disease relevance relation, wherein a lower relevance score indicates higher significance of the drug-disease relevance relation.

2. The terminal for analyzing the drug-disease relevance relation according to claim 1, wherein the processor is further configured to:

obtain a relevance score of the drug-disease relevance relation based on the pharmacodynamic relation model, to evaluate the drug-disease relevance relation.

3. The terminal for analyzing the drug-disease relevance relation according to claim 1, wherein an expression of the k-dimensional column vector dv for the drug, an expression of the k-dimensional column vector sv for the disease, an expression of the n-dimensional column vector vR for the drug-disease relevance relation, an expression of the n×k-dimensional mapping matrix $M_R$ for the drug-disease relevance relation, and an expression of the evaluation function f(d,r,s) for the drug-disease relevance relation are solved by optimizing a target function L;

$$L = \sum_{(di,r,sj) \in T} \sum_{(di',r,sj') \in T'} \max(0, f(di,r,sj) - f(di',r,sj') + \gamma)$$

where, $f(di, r, sj) = \|M_R \times dvi - M_R \times svj - vR\|_2$ $f(di', r, sj') = \|M_R \times dvi' - M_R \times svj' - vR\|_2$ where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max(a,b) represents an operation of taking a maximum value of a and b, and γ represents a pre-defined margin and γ≥f(di',r,sj')−f(di,r,sj).

4. The terminal for analyzing the drug-disease relevance relation according to claim 3, wherein a method for optimizing the target function L is a stochastic gradient descent algorithm.

5. The terminal for analyzing the drug-disease relevance relation according to claim 3, wherein k<n and both n and k are less than the number of types of drugs in the drug information and the number of types of diseases in the disease information.

6. The terminal for analyzing the drug-disease relevance relation according to claim 5, wherein the dimension of the real vector space is 300-500.

7. A method for analyzing a drug-disease relevance relation, which comprises:

collecting drug information, disease information and drug-disease relevance relation information, wherein the drug-disease relevance relation information comprises at least one of drug-disease therapeutic relation information and drug-disease side-effect relation information; and constructing a pharmacodynamic relation model based on the drug information, the disease information and the drug-disease relevance relation information, wherein the pharmacodynamic relation model is configured to analyze a drug-disease relevance relation r, and the drug-disease relevance relation comprises at least one of a drug-disease therapeutic relation $r_1$ and a drug-disease side-effect relation $r_0$, wherein after constructing the pharmacodynamic relation model, the method for analyzing the drug-disease relevance relation further comprises:

receiving drug information;

analyzing the drug information according to the pharmacodynamic relation model to obtain relevance relations between a drug in the drug information and different diseases, wherein the relevance relations between the drug in the drug information and different diseases comprise therapeutic relations between the drug in the drug information and different diseases and/or side-effect relations between the drug in the drug information and different diseases; and outputting the relevance relations between the drug in the drug information and different diseases; or, the method for analyzing the drug-disease relevance relation further comprises:

receiving disease information;

analyzing the disease information according to the pharmacodynamic relation model to obtain relevance relations between different drugs and a disease in the disease information, wherein the relevance relations between different drugs and the disease in the disease information comprise therapeutic relations between different drugs and the disease in the disease information and/or side-effect relations between different drugs and the disease in the disease information; and outputting the relevance relations between different drugs and the disease in the disease information; or, the method for analyzing the drug-disease relevance relation further comprises:

receiving drug information and disease information;

analyzing the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and outputting the relevance relation between the drug in the drug information and the disease in the disease information constructing the pharmacodynamic relation model based on the drug information, the disease information and the drug-disease relevance relation information comprises:

mapping the drug information, the disease information and the drug-disease relevance relation information to a real vector space to obtain vector space data, wherein the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, the n-dimensional column vector vR for the drug-disease relevance relation comprises an n-dimensional column vector vr for the drug-disease therapeutic relation and/or an n-dimensional column vector vs for the drug-disease side-effect relation, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation;

constructing an evaluation function f(d,r,s) for the drug-disease relevance relation according to the vector space data, and f(d,r,s)=$\|M_R \times dv - M_R \times sv - vR\|_2$, where d represents the drug, s represents the disease, and $\|.\|_2$ represents L2 norm, and wherein the pharmacodynamic relation is configured to provide recommendation with a relevance score of the drug-disease relevance relation, wherein a lower relevance score indicates higher significance of the drug-disease relevance relation.

8. The method for analyzing the drug-disease relevance relation according to claim 7, wherein setting a target function L according to the evaluation function f(d,r,s) for the drug-disease relevance relation, $$L = \sum_{(di,r,sj) \in T} \sum_{(di',r,sj') \in T'} \max(0, f(di, r, sj) - f(di', r, sj') + \gamma)$$

where, T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sr represents a disease without relevance; dvi' represents a k-dimensional column vector for the drug without correspondence, svj' represents a k-dimensional column vector for the disease without correspondence; max(a,b) represents an operation of taking a maximum value of a and b, and γ represents a pre-defined margin and γ≥f(di',r,sj')−f(di,r,sj);

optimizing the target function L to obtain presentation content of the vector space data; and obtaining an expression of the evaluation function f(d,r,s) for the drug-disease relevance relation according to the presentation content of the vector space data, wherein the presentation content of the vector space data and the expression of the evaluation function f(d,r,s) for the drug-disease relevance relation constitute the pharmacodynamic relation model.

9. The method for analyzing a drug-disease relevance relation according to claim 8, wherein a method for optimizing the target function L is a stochastic gradient descent algorithm.

10. The method for analyzing the drug-disease relevance relation according to claim 8, wherein k<n and both n and k are less than the number of types of drugs in the drug information and the number of types of diseases in the disease information.

11. The method for analyzing the drug-disease relevance relation according to claim 10, wherein the dimension of the real vector space is 300-500.

12. The method for analyzing the drug-disease relevance relation according to claim 8, wherein the evaluation function f(d,r,s) for the drug-disease relevance relation comprises an evaluation function f(d,r1,s) for the drug-disease therapeutic relation and/or an evaluation function f(d,r0,s) for the drug-disease side-effect relation, wherein $f(d,r1,s) = \|Mc \times dv - Mc \times sv - vr\|_2$ $f(d,r0,s) = \|Ms \times dv - Ms \times sv - vs\|_2$.

13. A non-transitory computer-readable storage medium storing executable instructions that, when executed by a terminal device, cause the terminal device to:

collect drug information, disease information and drug-disease relevance relation information, wherein the drug-disease relevance relation information comprises at least one of drug-disease therapeutic relation information and drug-disease side-effect relation information; and construct a pharmacodynamic relation model based on the drug information, the disease information and the drug-disease relevance relation information, wherein the pharmacodynamic relation model is configured to analyze a drug-disease relevance relation r, and the drug-disease relevance relation comprises at least one of a drug-disease therapeutic relation r1 and a drug-disease side-effect relation r0, wherein the executable instructions further causes the terminal device to perform operations selected from a group consisting of:

receiving drug information; analyzing the drug information according to the pharmacodynamic relation model to obtain relevance relations between a drug in the drug information and different diseases, wherein the relevance relation between the drug in the drug information and different diseases comprise therapeutic relations between the drug in the drug information and different diseases and/or side-effect relations between the drug in the drug information and different diseases; and outputting the relevance relations between the drug in the drug information and different diseases, receiving disease information; analyzing the disease information according to the pharmacodynamic relation model to obtain relevance relations between different drugs and a disease in the disease information, wherein the relevance relation between different drugs and the disease in the disease information comprise therapeutic relations between different drugs and the disease in the disease information and/or side-effect relations between different drugs and the disease in the disease information; and outputting the relevance relations between different drugs and the disease in the disease information, and receiving drug information and disease information; analyzing the drug information and the disease information according to the pharmacodynamic relation model to obtain a relevance relation between a drug in the drug information and a disease in the disease information, wherein the relevance relation between the drug in the drug information and the disease in the disease information comprises a therapeutic relation between the drug in the drug information and the disease in the disease information and/or a side-effect relation between the drug in the drug information and the disease in the disease information; and outputting the relevance relation between the drug in the drug information and the disease in the disease information, the pharmacodynamic relation model comprises an evaluation function f(d,r,s) for the drug-disease relevance relation and vector space data in a real vector space, $f(d,r,s)=\|M_R \times dv - M_R \times sv - vR\|_2$;

the vector space data comprises a k-dimensional column vector dv for a drug, a k-dimensional column vector sv for a disease, an n-dimensional column vector vR for the drug-disease relevance relation, and an n×k-dimensional mapping matrix $M_R$ for the drug-disease relevance relation, where d represents the drug, s represents the disease, $\|.\|2$ represents L2 norm, and the n×k-dimensional mapping matrix $M_R$ for the drug-disease relevance relation comprises an n×k-dimensional mapping matrix Mc for the drug-disease therapeutic relation and/or an n×k-dimensional mapping matrix Ms for the drug-disease side-effect relation; the n-dimensional column vector vR for the drug-disease relevance relation comprises an n-dimensional column vector yr for the drug-disease therapeutic relation and/or an n-dimensional column vector vs for the drug-disease side-effect relation, and wherein the pharmacodynamic relation is configured to provide recommendation with a relevance score of the drug-disease relevance relation, wherein a lower relevance score indicates higher significance of the drug-disease relevance relation.

14. The non-transitory computer-readable storage medium according to claim 13, wherein the executable instructions further cause the terminal device to:
obtain a relevance score of the drug-disease relevance relation based on the pharmacodynamic relation model, to evaluate the drug-disease relevance relation.

15. The non-transitory computer-readable storage medium according to claim 13, wherein
an expression of the k-dimensional column vector dv for the drug, an expression of the k-dimensional column vector sv for the disease, an expression of the n-dimensional column vector vR for the drug-disease relevance relation, an expression of the n×k-dimensional mapping matrix $M_R$ for the drug-disease relevance relation, and an expression of the evaluation function f(d,r,s) for the drug-disease relevance relation are solved by optimizing a target function L;

$$L = \sum_{(di,r,sj) \in T} \sum_{(di',r,sj') \in T'} \max(0, f(di, r, sj) - f(di', r, sj') + \gamma)$$

where, $$f(di, r, sj) = \|M_R \times dvi - M_R \times svj - vR\|_2$$

$$f(di', r, sj') = \|M_R \times dvi' - M_R \times svj' - vR\|_2$$

where T represents a set with relevance, T' represents a set without relevance, di represents a drug with relevance, sj represents a disease with relevance; dvi represents a k-dimensional column vector for the drug with correspondence, svj represents a k-dimensional column vector for the disease with correspondence; di' represents a drug without relevance, sj' represents a disease without relevance; dvi' represents a k-dimensional column vector for the drug without correspondence, svj' represents a k-dimensional column vector for the disease without correspondence; max(a,b) represents an operation of taking a maximum value of a and b, and γ represents a pre-defined margin and γ≥f(di',r,sj')−f(di,r,sj).

16. The non-transitory computer-readable storage medium according to claim 15, wherein a method for optimizing the target function L is a stochastic gradient descent algorithm.

17. The non-transitory computer-readable storage medium according to claim 15, wherein k<n and both n and k are less than the number of types of drugs in the drug information and the number of types of diseases in the disease information.

* * * * *